United States Patent
Baker et al.

(10) Patent No.: US 8,657,837 B2
(45) Date of Patent: Feb. 25, 2014

(54) TISSUE FIXATION DEVICES AND A TRANSORAL ENDOSCOPIC GASTROESOPHAGEAL FLAP VALVE RESTORATION DEVICE AND ASSEMBLY USING SAME

(75) Inventors: Steve G. Baker, Redmond, WA (US); Brett J. Carter, Monroe, WA (US); Stefan J.M. Kraemer, Seattle, WA (US); Clifton A. Alferness, Redmond, WA (US); John M. Adams, Sammamish, WA (US)

(73) Assignee: EndoGastric Solutions, Inc., Redmond, WA (US)

( * ) Notice: Subject to any disclaimer, the term of this patent is extended or adjusted under 35 U.S.C. 154(b) by 379 days.

(21) Appl. No.: 12/460,510

(22) Filed: Jul. 18, 2009

(65) Prior Publication Data
US 2010/0030243 A1 Feb. 4, 2010

Related U.S. Application Data

(63) Continuation of application No. 10/783,717, filed on Feb. 20, 2004, now abandoned.

(51) Int. Cl.
*A61B 17/08* (2006.01)

(52) U.S. Cl.
USPC .......................................................... 606/151

(58) Field of Classification Search
USPC ........... 606/151, 213, 139, 157, 232; 600/585
See application file for complete search history.

(56) References Cited

U.S. PATENT DOCUMENTS

| | | | | |
|---|---|---|---|---|
| 4,006,747 A | * | 2/1977 | Kronenthal et al. | 606/144 |
| 4,669,473 A | * | 6/1987 | Richards et al. | 606/215 |
| 4,696,300 A | * | 9/1987 | Anderson | 606/219 |
| 5,411,520 A | * | 5/1995 | Nash et al. | 606/213 |
| 5,879,372 A | * | 3/1999 | Bartlett | 606/232 |
| 6,666,872 B2 | * | 12/2003 | Barreiro et al. | 606/142 |
| 2004/0133236 A1 | * | 7/2004 | Chanduszko | 606/213 |

* cited by examiner

*Primary Examiner* — Corrine M McDermott
*Assistant Examiner* — Son Dang
(74) *Attorney, Agent, or Firm* — Fulwider Patton LLP

(57) ABSTRACT

Tissue fasteners carried on a tissue piercing deployment wire fasten tissue layers of a mammalian body together. The fasteners include a first member, a second member, and a connecting member extending between the first and second members. The first and second members are substantially parallel to each other. The fasteners may be deployed in limited spaces and in various applications including the restoration of a gastroesophageal flap valve.

14 Claims, 16 Drawing Sheets

TISSUE FIXATION DEVICES AND A TRANSORAL ENDOSCOPIC GASTROESOPHAGEAL FLAP VALVE RESTORATION DEVICE AND ASSEMBLY USING SAME

This application is a continuation application of U.S. application Ser. No. 10/783,717, filed on Feb. 20, 2004, which is abandoned. The entire disclosure of which is hereby incorporated for all purposes.

FIELD OF THE INVENTION

The present invention generally relates to tissue fixation devices, and more particularly to devices for treating gastroesophageal reflux disease using the same. The present invention more particularly relates to such tissue fixation devices which may be used in surgical environments and which are self-deploying.

BACKGROUND

Gastroesophageal reflux disease (GERD) is a chronic condition caused by the failure of the anti-reflux barrier located at the gastroesophageal junction to keep the contents of the stomach from splashing into the esophagus. The splashing is known as gastroesophageal reflux. The stomach acid is designed to digest meat, and will digest esophageal tissue when persistently splashed into the esophagus.

A principal reason for regurgitation associated with GERD is the mechanical failure of a deteriorated gastroesophageal flap to close and seal against high pressure in the stomach. Due to reasons including lifestyle, a Grade I normal gastroesophageal flap may deteriorate into a malfunctioning Grade III or absent valve Grade IV gastroesophageal flap. With a deteriorated gastroesophageal flap, the stomach contents are more likely to be regurgitated into the esophagus, the mouth, and even the lungs. The regurgitation is referred to as "heartburn" because the most common symptom is a burning discomfort in the chest under the breastbone. Burning discomfort in the chest and regurgitation (burping up) of sour-tasting gastric juice into the mouth are classic symptoms of gastroesophageal reflux disease (GERD). When stomach acid is regurgitated into the esophagus, it is usually cleared quickly by esophageal contractions. Heartburn (backwashing of stomach acid and bile onto the esophagus) results when stomach acid is frequently regurgitated into the esophagus and the esophageal wall is inflamed.

Complications develop for some people who have GERD. Esophagitis (inflammation of the esophagus) with erosions and ulcerations (breaks in the lining of the esophagus) can occur from repeated and prolonged acid exposure. If these breaks are deep, bleeding or scarring of the esophagus with formation of a stricture (narrowing of the esophagus) can occur. If the esophagus narrows significantly, then food sticks in the esophagus and the symptom is known as dysphagia. GERD has been shown to be one of the most important risk factors for the development of esophageal adenocarcinoma. In a subset of people who have severe GERD, if acid exposure continues, the injured squamous lining is replaced by a precancerous lining (called Barrett's Esophagus) in which a cancerous esophageal adenocarcinoma can develop.

Other complications of GERD may not appear to be related to esophageal disease at all. Some people with GERD may develop recurrent pneumonia (lung infection), asthma (wheezing), or a chronic cough from acid backing up into the esophagus and all the way up through the upper esophageal sphincter into the lungs. In many instances, this occurs at night, while the person is in a supine position and sleeping. Occasionally, a person with severe GERD will be awakened from sleep with a choking sensation. Hoarseness can also occur due to acid reaching the vocal cords, causing a chronic inflammation or injury.

GERD never improves without intervention. Life style changes combined with both medical and surgical treatments exist for GERD. Medical therapies include antacids and proton pump inhibitors. However, the medical therapies only mask the reflux. Patients still get reflux and perhaps emphysema because of particles refluxed into the lungs. Barrett's esophagus results in about 10% of the GERD cases. The esophageal epithelium changes into tissue that tends to become cancerous from repeated acid washing despite the medication.

Several open laparotomy and laproscopic surgical procedures are available for treating GERD. One surgical approach is the Nissen fundoplication. The Nissen approach typically involves a 360-degree wrap of the fundus around the gastroesophageal junction. The procedure has a high incidence of postoperative complications. The Nissen approach creates a 360-degree moveable flap without a fixed portion. Hence, Nissen does not restore the normal movable flap. The patient cannot burp because the fundus was used to make the repair, and may frequently experience dysphagia. Another surgical approach to treating GERD is the Belsey Mark IV (Belsey) fundoplication. The Belsey procedure involves creating a valve by suturing a portion of the stomach to an anterior surface of the esophagus. It reduces some of the postoperative complications encountered with the Nissen fundoplication, but still does not restore the normal movable flap. None of these procedures fully restores the normal anatomical anatomy or produces a normally functioning gastroesophageal junction. Another surgical approach is the Hill repair. In the Hill repair, the gastroesophageal junction is anchored to the posterior abdominal areas, and a 180-degree valve is created by a system of sutures. The Hill procedure restores the moveable flap, the cardiac notch and the Angle of His. However, all of these surgical procedures are very invasive, regardless of whether done as a laproscopic or an open procedure.

New, less surgically invasive approaches to treating GERD involve transoral endoscopic procedures. One procedure contemplates a machine device with robotic arms that is inserted transorally into the stomach. While observing through an endoscope, an endoscopist guides the machine within the stomach to engage a portion of the fundus with a corkscrew-like device on one arm. The arm then pulls on the engaged portion to create a fold of tissue or radial plication at the gastroesophageal junction. Another arm of the machine pinches the excess tissue together and fastens the excess tissue with one pre-tied implant. This procedure does not restore normal anatomy. The fold created does not have anything in common with a valve. In fact, the direction of the radial fold prevents the fold or plication from acting as a flap of a valve.

Another transoral procedure contemplates making a fold of fundus tissue near the deteriorated gastroesophageal flap to recreate the lower esophageal sphincter (LES). The procedure requires placing multiple U-shaped tissue clips around the folded fundus to hold it in shape and in place.

This and the previously discussed procedure are both highly dependent on the skill, experience, aggressiveness, and courage of the endoscopist. In addition, these and other procedures may involve esophageal tissue in the repair. Esophageal tissue is fragile and weak. Involvement of esophageal tissue in the repair of a gastroesophageal flap valve poses unnecessary risks to the patient.

A new and improved apparatus and method for restoration of a gastroesophageal flap valve is fully disclosed in copending U.S. application Ser. No. 10/150,740, filed May 17, 2002, for TRANSORAL ENDOSCOPIC GASTROESOPHAGEAL FLAP VALVE RESTORATION DEVICE, ASSEMBLY, SYSTEM AND METHOD, is assigned to the assignee of this invention, and is incorporated herein by reference. That apparatus and method provides a transoral endoscopic gastroesophageal flap valve restoration. A longitudinal member arranged for transoral placement into a stomach carries a tissue shaper that non-invasively grips and shapes stomach tissue. A tissue fixation device is then deployed to maintain the shaped stomach tissue in a shape approximating a gastroesophageal flap.

Whenever tissue is to be maintained in a shape as, for example, in the improved assembly last mentioned above, it is necessary to fasten at least two layers of tissue together. In applications such as gastroesophageal flap valve restoration, there is very limited room to maneuver a fastener deployment device. For example, this and other medical fastening applications provide confined working channels and spaces and often must be fed through an endoscope to permit visualization or other small lumen guide catheters to the place where the fasteners are to be deployed. To make matters worse, multiple fasteners may also be required. Hence, with current fasteners and deployment arrangements, it is often difficult to direct a single fastener to its intended location, let alone a number of such fasteners.

Once the fastening site is located, the fasteners employed must be truly able to securely maintain the tissue. Also, quite obviously, the fasteners are preferably deployable in the tissue in a manner which does not unduly traumatize the tissue.

SUMMARY

The present invention provides a fastener for use in a mammalian body, comprising a first member, a second member, the first and second members having first and second ends, and a connecting member fixed to each of the first and second members intermediate the first and second ends and extending between the first and second members. The first and second members are separated by the connecting member, and one of the first and second members has a longitudinal axis and a through channel along the axis arranged to be slidingly received on a tissue piercing deployment wire.

The connecting member may be flexible permitting another one of the first and second members to be next to the one of the first and second members when the one of the first and second members is on the tissue piercing deployment wire.

One end of the one of the first and second members may include a pointed tip. The pointed tip may be conical or comprise a tapered sectioned portion.

Both the first and second members may include a longitudinal axis and a through channel along each respective axis. One end of both the first and second members may include a pointed tip. The pointed tips may point in opposite directions.

The through channels are arranged to be slidingly received by the tissue piercing deployment wire. The connecting member may be flexible permitting the first and second members to be in line with each other on the tissue piercing deployment wire.

The first member, second member, and the connecting member may all be formed of plastic material and in one piece or multiple pieces.

The connecting member of the fastener may be formed of plastic elastic material. Alternatively, the connecting member may be formed of a plastic, permanently deformable material. The plastic material may include a color pigment contrasting with body tissue color to enable visualization of the fastener with an endoscope.

The connecting member has a vertical dimension and a horizontal dimension transverse to the vertical dimension, and the horizontal dimension may be substantially less than the vertical dimension rendering the connecting member readily bendable in a horizontal plane. At least one of the first and second members may include a plurality of longitudinally spaced vertical slots rendering the at least one of the first and second members flexible in a direction opposite the slots but stiff in a direction of the slots. The device may comprise a plurality of the connecting members.

The fastener may alternatively be formed of metal and particularly a shape memory material. The first and second members may then be self-deployable. One of the first and second members may be self-deployable while on the tissue piercing deployment wire.

At least one of the first and second members may be self-deployable upon removal from the tissue piercing deployment wire. The at least one of the first and second members is preferably distal to another one of the first and second members and the another one of the first and second members may include a crimp that provides a controlled resistance to movement on the tissue piercing deployment wire.

The first member, the second member, and the connecting member may be integrally formed from a same tubular member stock. The connecting member may comprise a strip of the tubular member formed by a pair of longitudinal substantially parallel, substantially coextensive cuts within the tubular member and the first and second members may be formed by a substantially transverse circumferential cut between the substantially parallel coextensive cuts.

The tubular member may have first and second opposed ends and the substantially parallel substantially coextensive cuts may begin spaced from the first end and terminate spaced from the second end. The first and second members may then be tubular member sections between the circumferential cut and the tubular member first and second ends. An elongated notch may extend from one of the ends of the tubular member, substantially diametrically opposite and juxtaposed to a portion of the connecting member strip.

The invention further provides a fastener assembly for use in a mammalian body. The assembly includes a fastener including a first member, a second member, the first and second members having first and second ends, and a connecting member fixed to each of the first and second members intermediate the first and second ends and extending between the first and second members. The first and second members are separated by the connecting member, and one of the first and second members may have a longitudinal axis and a through channel along the axis. The assembly further includes a deployment wire that slidingly receives the through channel of the one of the first and second members and pierces into the tissue, and a pusher that pushes the one of first and second members into the tissue while on the deployment wire.

The pusher is preferably also arranged to be slidingly received on the deployment wire. The connecting member of the fastener may be flexible, and the assembly may further comprise a guide tube extending over the deployment wire and the fastener. The other one of the first and second members may be disposed next to the one of the first and second members within the guide tube.

One end of the one of the first and second members of the fastener may further include a pointed tip. The pointed tip may comprise a truncated cone. Alternatively, the pointed tip may comprise a sectioned portion. Either one or both of the first and second members may include a longitudinal axis and a through channel along each respective axis. The through channels of the first and second members may be arranged to be slidingly received by the tissue piercing deployment wire and the connecting member is preferably flexible permitting the first and second members to be in line with each other on the tissue piercing deployment wire. The guide tube may then extend over the deployment wire and the fastener.

The invention still further provides a tissue fixation assembly. The assembly includes a fastener and a pair of hingedly coupled first and second arms for receiving the tissue therebetween. The first arm includes a fastener director that directs the fastener into the tissue and the second arm includes an opening permitting the fastener to be driven through the tissue while being held between the first and second arms. The second arm is preferably a frame structure.

The assembly may further comprise a tissue gripper that grips the tissue and pulls the tissue into and between the first and second arms. The first arm may have a tissue engaging surface and the fastener director may include a channel communicating with the tissue engaging surface through which the fastener passes into the tissue.

The fastener director may include a plurality of the channels to direct a like plurality of fasteners into the tissue. The assembly may further comprise a fastener deployment wire that guides the fastener through one of the channels and into the tissue.

The fastener of the assembly may comprise a first member, a second member, the first and second members having first and second ends, and a connecting member fixed to each of the first and second members intermediate the first and second ends and extending between the first and second members. The first and second members are separated by the connecting member when the fastener is deployed. One of the first and second members preferably has a longitudinal axis and a through channel along the axis arranged to be slidingly received on the fastener deployment wire.

The invention still further provides a transoral gastroesophageal flap valve restoration device. The device includes a longitudinal member, a portion of which is arranged for transoral placement into a stomach, a fastener, and a tissue shaper carried on the longitudinal member. The tissue shaper shapes stomach tissue into a shape and includes a pair of hingedly coupled first and second arms for receiving the stomach tissue therebetween, the first arm including a fastener director that directs the fastener into the stomach tissue and the second arm including an opening permitting the fastener to be driven through the stomach tissue while being held between the first and second arms.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like referenced numerals identify like elements, and wherein:

DETAILED DESCRIPTION

Figure 1:
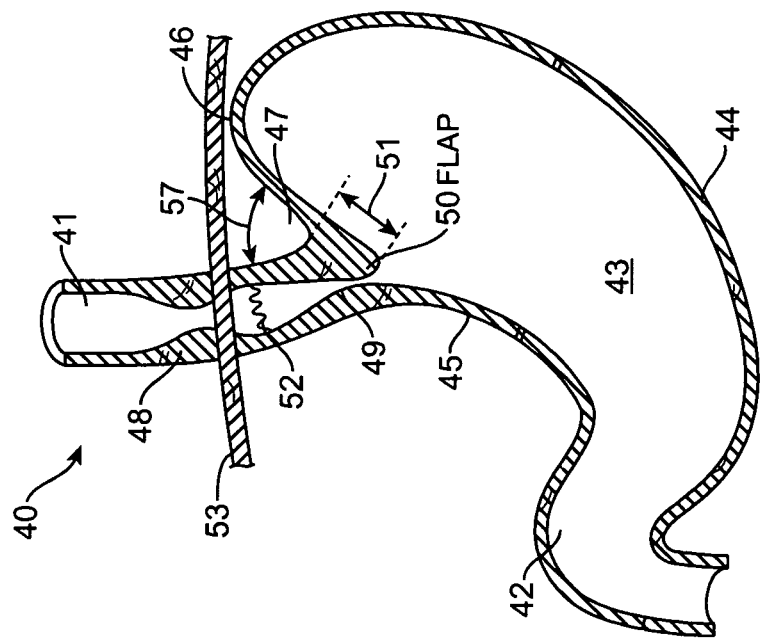
FIG. 1 is a front cross-sectional view of the esophageal-gastro-intestinal tract from a lower portion of the esophagus to the duodenum.

FIG. 1 is a front cross-sectional view of the esophageal-gastro-intestinal tract 40 from a lower portion of the esophagus 41 to the duodenum 42. The stomach 43 is characterized by the greater curvature 44 on the anatomical left side and the lesser curvature 45 on the anatomical right side. The tissue of the outer surfaces of those curvatures is referred to in the art as serosa tissue. As will be seen subsequently, the nature of the serosa tissue is used to advantage for its ability to bond to like serosa tissue. The fundus 46 of the greater curvature 44 forms the superior portion of the stomach 43, and traps gas and air bubbles for burping. The esophageal tract 41 enters the stomach 43 at an esophageal orifice below the superior portion of the fundus 46, forming a cardiac notch 47 and an acute angle with respect to the fundus 46 known as the Angle of His 57. The lower esophageal sphincter (LES) 48 is a discriminating sphincter able to distinguish between burping gas, liquids, and solids, and works in conjunction with the fundus 46 to burp. The gastroesophageal flap valve (GEFV) 49 includes a moveable portion and an opposing more stationary portion. The moveable portion of the GEFV 49 is an approximately 180 degree, semicircular, gastroesophageal flap 50 (alternatively referred to as a "normal moveable flap" or "moveable flap") formed of tissue at the intersection between the esophagus 41 and the stomach 43. The opposing more stationary portion of the GEFV 49 comprises a portion of the lesser curvature 45 of the stomach 43 adjacent to its junction with the esophagus 41. The gastroesophageal flap 50 of the GEFV 49 principally comprises tissue adjacent to the fundus 46 portion of the stomach 43, is about 4 to 5 cm long (51) at it longest portion, and the length may taper at its anterior and posterior ends. The gastroesophageal flap 50 is partially held against the lesser curvature 45 portion of the stomach 43 by the pressure differential between the stomach 43 and the thorax, and partially by the resiliency and the anatomical structure of the GEFV 49, thus providing the valving function. The GEFV 49 is similar to a flutter valve, with the gastroesophageal flap 50 being flexible and closeable against the other more stationary side.

The esophageal tract is controlled by an upper esophageal sphincter (UES) in the neck near the mouth for swallowing, and by the LES 48 and the GEFV 49 at the stomach. The normal anti-reflux barrier is primarily formed by the LES 48 and the GEFV 49 acting in concert to allow food and liquid to enter the stomach, and to considerably resist reflux of stomach contents into the esophagus 41 past the gastroesophageal tissue junction 52. Tissue aboral of the gastroesophageal tissue junction 52 is generally considered part of the stomach because the tissue protected from stomach acid by its own protective mechanisms. Tissue oral of the gastroesophageal junction 52 is generally considered part of the esophagus and it is not protected from injury by prolonged exposure to stomach acid. At the gastroesophageal junction 52, the juncture of the stomach and esophageal tissues form a zigzag line, which is sometimes referred to as the "Z-line." For the purposes of these specifications, including the claims, "stomach" means the tissue aboral of the gastroesophageal junction 52.

Figure 2:
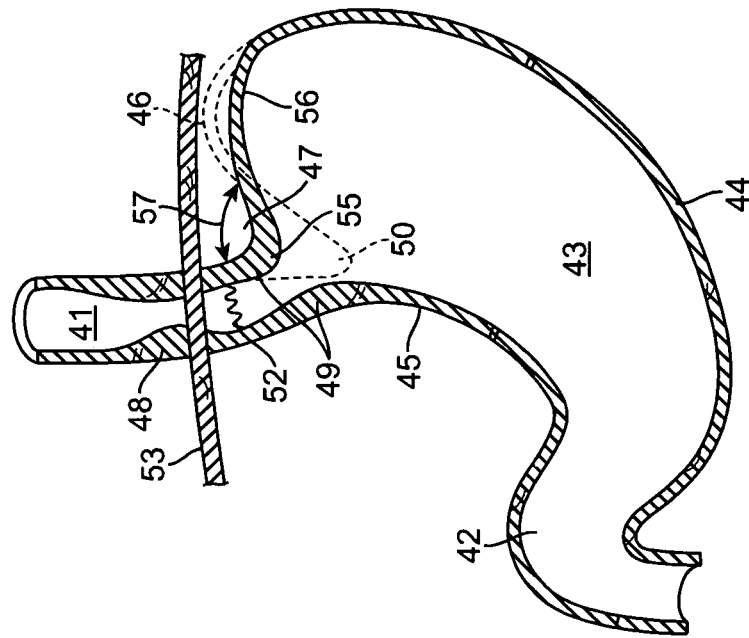
FIG. 2 is a front cross-sectional view of the esophageal-gastro-intestinal tract illustrating a Grade I normal appearance movable flap of the gastroesophageal flap valve (in dashed lines) and a Grade III reflux appearance gastroesophageal flap of the gastroesophageal flap valve (in solid lines)

FIG. 2 is a front cross-sectional view of an esophageal-gastro-intestinal tract illustrating a Grade I normal appearance movable flap 50 of the GEFV 49 (shown in dashed lines) and a deteriorated Grade III gastroesophageal flap 55 of the GEFV 49 (shown in solid lines). As previously mentioned, a principal reason for regurgitation associated with GERD is the mechanical failure of the deteriorated (or reflux appearance) gastroesophageal flap 55 of the GEFV 49 to close and seal against the higher pressure in the stomach. Due to reasons including lifestyle, a Grade I normal gastroesophageal flap 50 of the GEFV 49 may deteriorate into a Grade III deteriorated gastroesophageal flap 55. The anatomical results of the deterioration include moving a portion of the esophagus 41 that includes the gastroesophageal junction 52 and LES 48 toward the mouth, straightening of the cardiac notch 47, and increasing the Angle of His 57. This effectively reshapes the anatomy aboral of the gastroesophageal junction 52 and forms a flattened fundus 56. The deteriorated gastroesophageal flap 55 illustrates a gastroesophageal flap valve 49 and cardiac notch 47 that have both significantly degraded. Dr. Hill and colleagues developed a grading system to describe the appearance of the GEFV and the likelihood that a patient will experience chronic acid reflux. L. D. Hill, et al., *The gastroesophageal flap valve: in vitro and in vivo observations*, Gastrointestinal Endoscopy 1996: 44:541-547. Under Dr. Hill's grading system, the normal movable flap 50 of the GEFV 49 illustrates a Grade I flap valve that is the least likely to experience reflux. The deteriorated gastroesophageal flap 55 of the GEFV 49 illustrates a Grade III (almost Grade IV) flap valve. A Grade IV flap valve is the most likely to experience reflux. Grades II and III reflect intermediate grades of deterioration and, as in the case of III, a high likelihood of experiencing reflux. With the deteriorated GEFV represented by deteriorated gastroesophageal flap 55 and the fundus 46 moved inferior, the stomach contents are presented a funnel-like opening directing the contents into the esophagus 41 and the greatest likelihood of experiencing reflux. Disclosed subsequently is a device for restoring the normal gastroesophageal flap valve anatomy, which device is one embodiment of the present invention.

Figure 3:
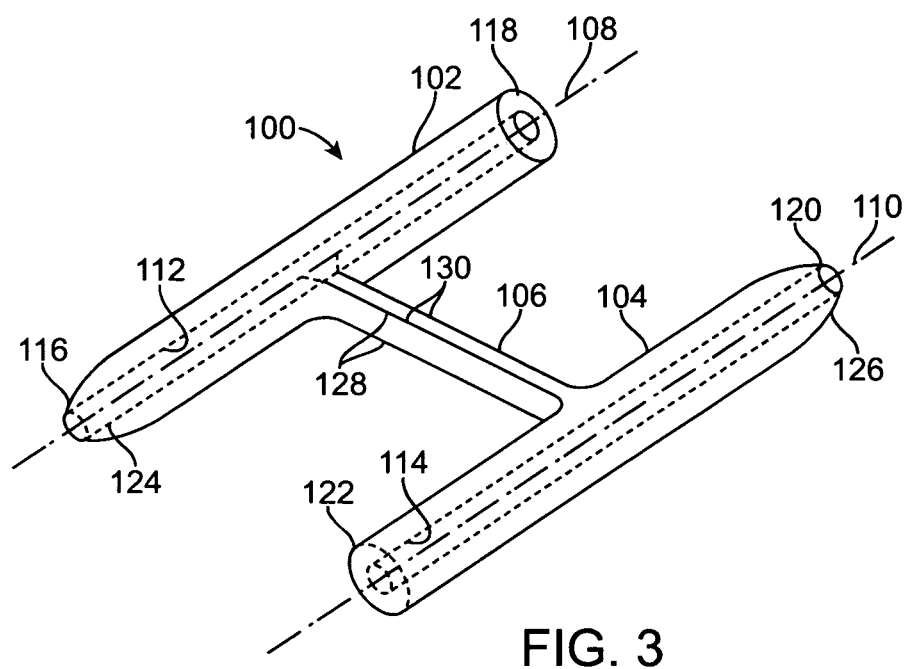
FIG. 3 is a perspective view of a fastener according to an embodiment of the invention.

Referring now to FIG. 3, it is a perspective view of a fastener 100 according to an embodiment of the invention. The fastener 100 generally includes a first member 102, a second member 104, and a connecting member 106. As may be noted in FIG. 3, the first member 102 and second member 104 are substantially parallel and substantially perpendicular to the connecting member 106 which connects the first member 102 to the second member 104.

The first and second members 102 and 104 are generally cylindrical. Each has a longitudinal axis 108 and 110 and a through channel 112 and 114 along the longitudinal axes 108 and 110. The through channels 112 and 114 are formed by through bores which are dimensioned to be slidingly received on a tissue piercing deployment wire to be described hereinafter.

The first member 102 also includes a first end 116 and a second end 118. Similarly, the second member 114 includes a first end 120 and a second end 122. The first ends 116 and 120 form pointed dilation tips 124 and 126, respectively. The dilation tips 124 and 126 are conical and more particularly take the shape of truncated cones. The pointed tips 129 and 126 are pointed in opposite directions.

The first and second members 102 and 104 and the connecting 106 may be formed of different materials and have different textures. These materials may include, for example, plastic materials such as polypropylene, polyethylene, polyglycolic acid, polyurethane, or a thermoplastic elastomer. As may be further noted in FIG. 3, the connecting member 106 has a vertical dimension 128 and a horizontal dimension 130 which is transverse to the vertical dimension. The horizontal dimension is substantially less than the vertical dimension to render the connecting member 106 readily bendable in a horizontal plane. The connecting member is further rendered bendable by the nature of the plastic material from which the fastener 100 is formed. The connecting member may be formed from either an elastic plastic or a permanently deformable plastic. An elastic material would prevent compression necrosis in some applications.

Figure 4:
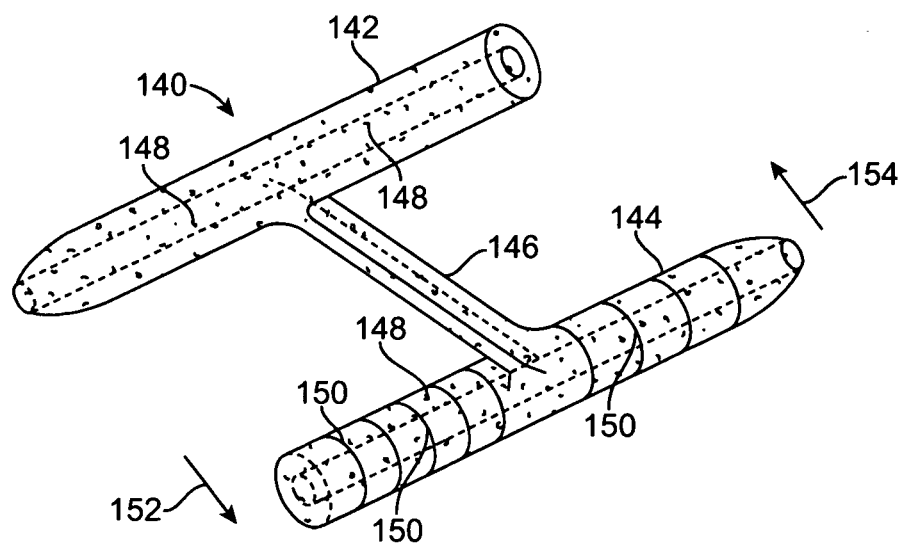
FIG. 4 is a perspective view of another fastener according to an embodiment of the invention.

Referring now to FIG. 4, it illustrates another fastener 140 embodying the present invention. As with the fastener 100 of FIG. 3, the fastener 140 includes a first member 142, a second member 144, and a connecting member 146. The fastener 140 may be formed in one piece and a plastic material similar to the fastener 100 of FIG. 3. The fasteners 100 and 140 may be formed of a plastic material which includes a color pigment, for example pthalocyanine blue, for contrasting with the color of body tissue to enable visualization of the fastener with an endoscope during the deployment of the fasteners. In addition, as may be seen in FIG. 4, the fastener 140 is impregnated with radio opaque material 148 so as to render the fastener 140 at least partially viewable under fluoroscopy. The radio opaque particles may be, for example, barium sulfate, bismuth subcarbonate, tungsten powder or tantalum powder.

In addition to the foregoing, the second member 144 of the fastener 140 includes a plurality of longitudinally spaced vertical slots 150. This renders the second member 144 flexible in a direction opposite the slots but stiff in a direction of the slots. Hence, the second member 144 is resistant to bending in a first direction indicated by arrow 152 while being substantially less resistant to bending in a direction indicated by arrow 154. The reduced resistance to bending in the direction 154 of the second member 144 of the fastener 140 may be utilized to advantage in the deployment of the fastener 140.

Figure 5:
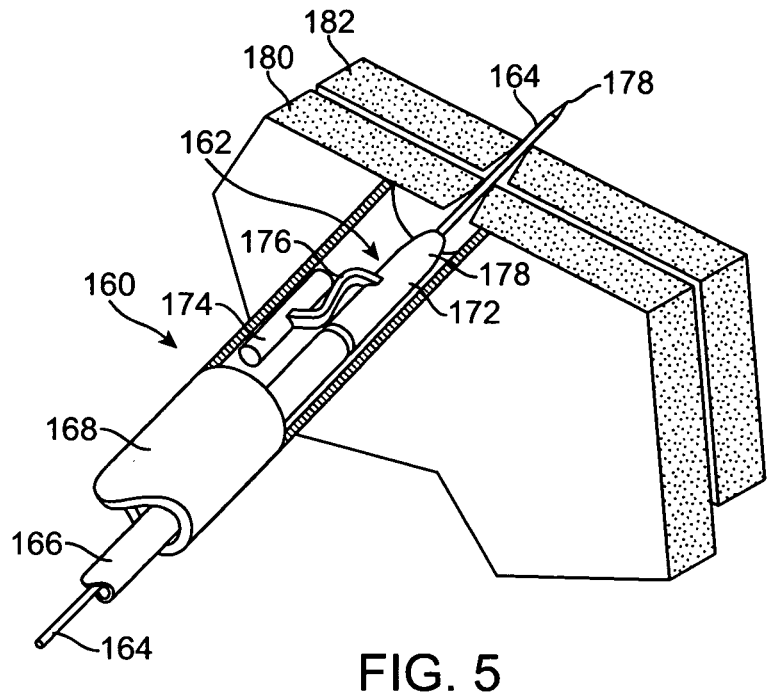
FIG. 5 is a perspective view with portions cut away of a fastener assembly according to an embodiment of the invention in an early stage of deploying a fastener embodiment of the invention.

Referring now to FIG. 5, it is a perspective view with portions cut away of a fastener assembly embodying the present invention. The tissue layer portions above the fastener 162 have been shown cut away in FIGS. 5-9 to enable the deployment procedure to be seen more clearly. The assembly 160 generally includes a fastener 162, a deployment wire 164, a pusher 166, and a guide tube 168.

The fastener 162 takes the form of a further fastener embodiment of the present invention and includes a first member 172, a second member 174, and a connecting member 176. The fastener 162 differs from the fasteners 100 and 140 of FIGS. 3 and 4, respectively, in that the second member 174 is of solid construction and does not include a longitudinal through channel or a pointed tip. However, the first member 172 includes a through channel as previously described and a pointed tip 178.

The first member 172 of the fastener 162 is slidingly received on the deployment wire 164. The deployment wire 164 has a pointed tip 178 for piercing the tissue layers 180 and 182 to be fastened together. As will be seen hereinafter, and in accordance with further aspects of the present invention, the tissue layers 180 and 182 may be folded stomach tissue which are to be fastened and maintained together to form and maintain a gastroesophageal flap valve.

As will be noted in FIG. 5, the tissue piercing wire 164, fastener 162, and the pusher 166 are all within the guide tube 168. The guide tube 168 may take the form of a catheter, for example.

As will be further noted in FIG. 5, the second member 174 is disposed along side the first member 172. This is rendered possible by the flexibility of the connecting member 176. Preferably, the first member, connecting member, and second member are arranged so that the connecting member 176 lies to the side of the first member 172 and the second member 174.

With the first member 172 of the fastener 162 slidingly received on the tissue piercing wire 164 and with the pusher 166 just touching the first member 172 on the tissue piercing wire 164, the tip 178 of the tissue piercing wire 164 pierces the tissue layers 180 and 182. The subassembly of the tissue piercing wire 164, fastener 162, and pusher 166 may be guided to its intended location relative to the tissue layers 180 and 182 by the guide tube 168. As will be seen hereinafter, this subassembly may be alternatively guided by guide channels arranged to accommodate the tissue piercing wire 164, fastener 162, pusher 166, and the guide tube 168.

Figure 6:
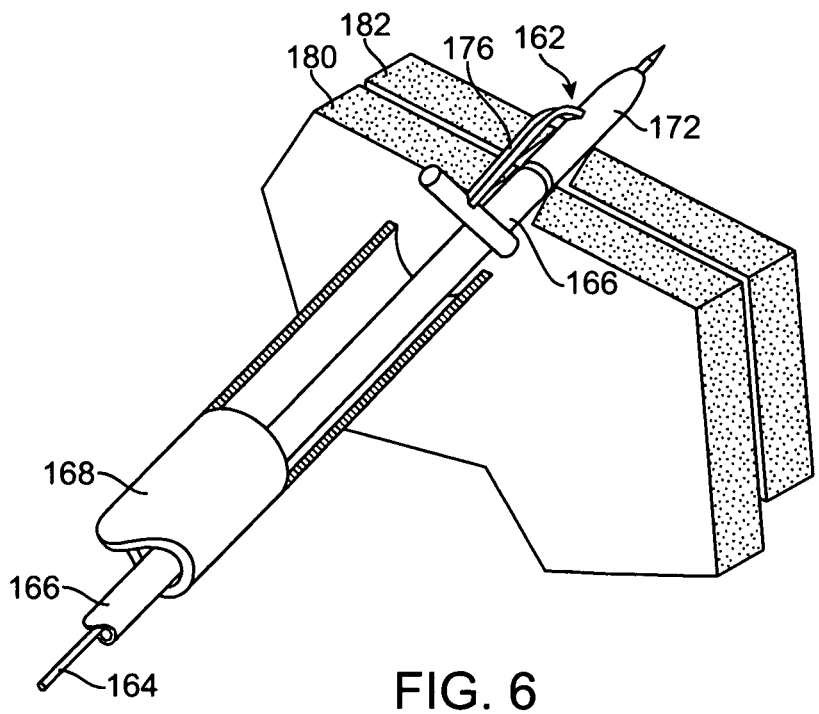
FIG. 6 is a perspective view of the assembly of FIG. 5 shown with the fastener being driven in the tissue layers to be fastened.
Figure 7:
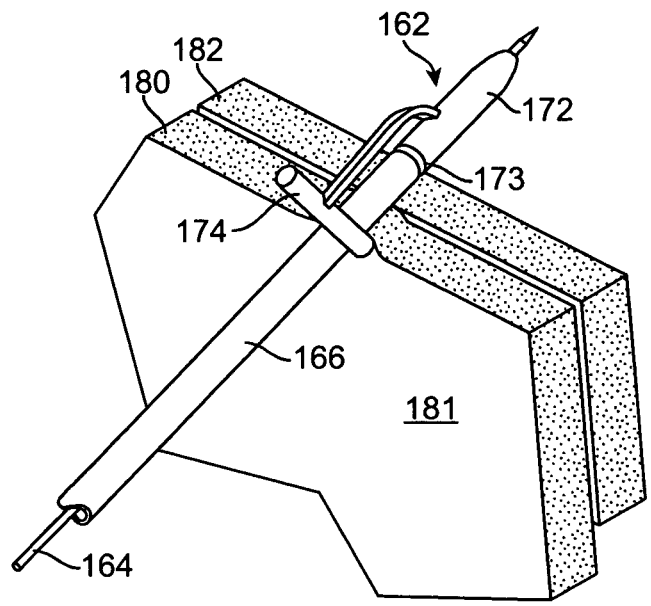
FIG. 7 is a perspective view of the assembly of FIG. 5 shown with the fastener extending through the tissue layers to be fastened.

Once the tissue piercing wire 164 has pierced the tissue layers 180 and 182 to be fastened together, the pusher 166 may be utilized to push the first member 172 of the fastener 162 through the tissue layers 180 and 182 on the tissue piercing wire 164. This is illustrated in FIG. 6. As the pusher 166 pushes the first member 172 through the tissue layers 180 and 182, the connecting member 176 follows along beside and immediately adjacent to the first member 172 of the fastener 162 and the pusher 166. As may be seen in FIG. 7, the pusher 166 continues to push the first member 172 of the fastener 162 through the tissue layers 180 and 182 on the tissue piercing wire 164 until the end 173 of the first member 172 engaging the pusher 166 clears the second tissue layer 182. It may also be noted that at this time, the second member 174 of the fastener 162 has engaged the surface 181 of tissue layer 180.

Figure 8:
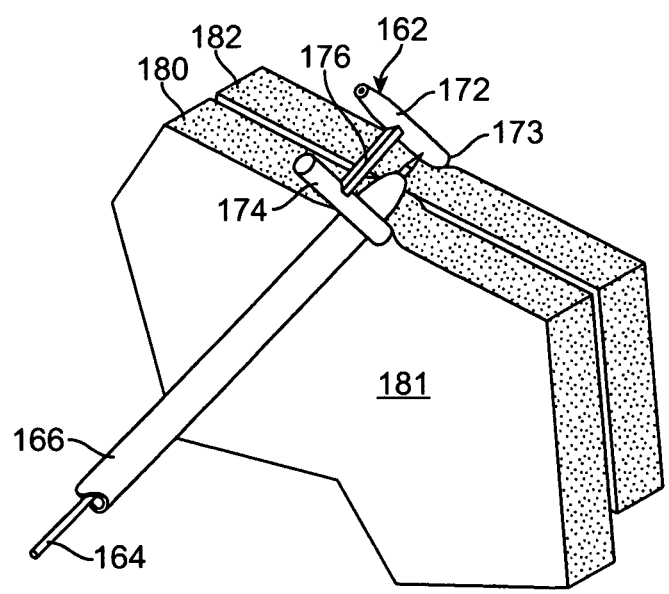
FIG. 8 is a perspective view of the assembly of FIG. 5 shown with the fastener initially deployed.

Referring now to FIG. 8, it will be seen that once the end 173 of the first member 172 has cleared the tissue layer 182, the tissue piercing wire 164 is then retracted within the pusher 166 to release the first member 172. The first member 172 being thus released from the tissue piercing wire 164 will return to its original configuration substantially parallel to the second member 174 and substantially perpendicular to the connecting member 176. When the first member 172 is deployed as shown in FIG. 8, the tissue piercing wire 164 and pusher 166 may be withdrawn.

Figure 9:
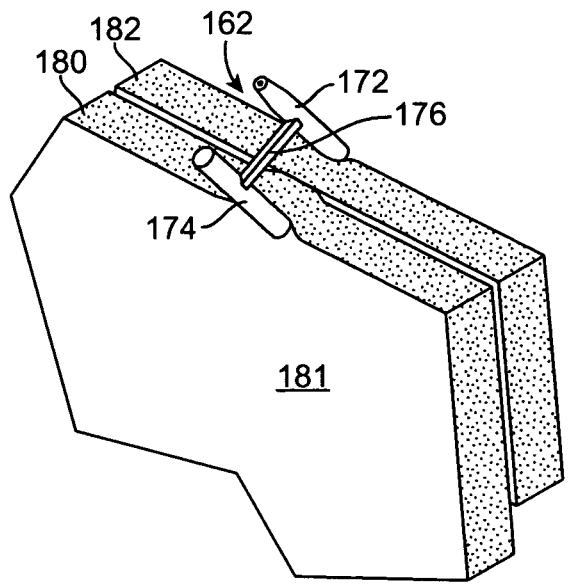
FIG. 9 is a perspective view showing the fastener of the assembly of FIG. 5 fully deployed and securely fastening a pair of tissue layers together.

FIG. 9 illustrates the fastener 162 in its deployed position. It will be noted that the tissue layers 180 and 182 are fastened together between the first member 172 of the fastener 162 and the second member 174 of the fastener 162. The connecting member 176 extends through the tissue layers 180 and 182.

Figure 10:
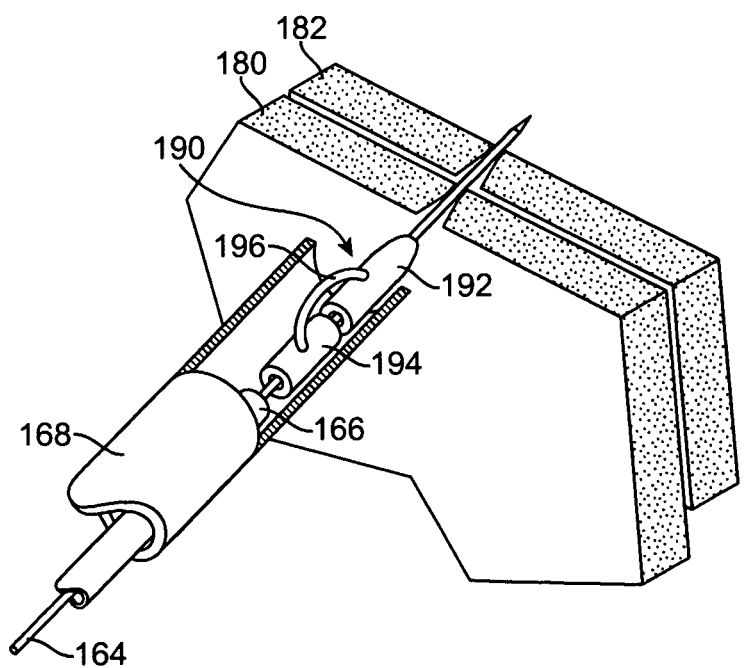
FIG. 10 is a perspective view with portions cut away of another fastener deployment assembly according to an embodiment of the invention in an early stage of deploying another fastener embodiment of the invention.

FIG. 10 is a perspective view with portions cut away of another fastener and fastener assembly embodying the present invention in an early stage of deploying the fastener. The fastener 190 of FIG. 10 includes a first member 192, a second member 194, and a connecting member 196. The fastener 190 is similar to the fastener 100 of FIG. 3 in that both the first member 192 and second member 194 includes a through bore. This permits the first member 192 and second member 194 to be slidingly received in line with each other on the tissue piercing wire 164. With both the first member 192 and second member 194 being disposed on the tissue piercing wire 164, the second member 194 will not be deployed until after the tissue piercing wire 164 is retracted from the second member 194. As a result, the second member of the fastener 162 illustrated in FIGS. 5-9 will deploy before the second member 194 of fastener 190. However, the arrangement illustrated in FIG. 10 may be advantageous where space is at a premium and the guide tube 168 has a reduced diameter. The deployment of the fastener 190 by the tissue piercing wire 164, the pusher 166, and the guide tube 168 is otherwise similar to the deployment procedure described above with respect to FIGS. 5-9.

Figure 11:
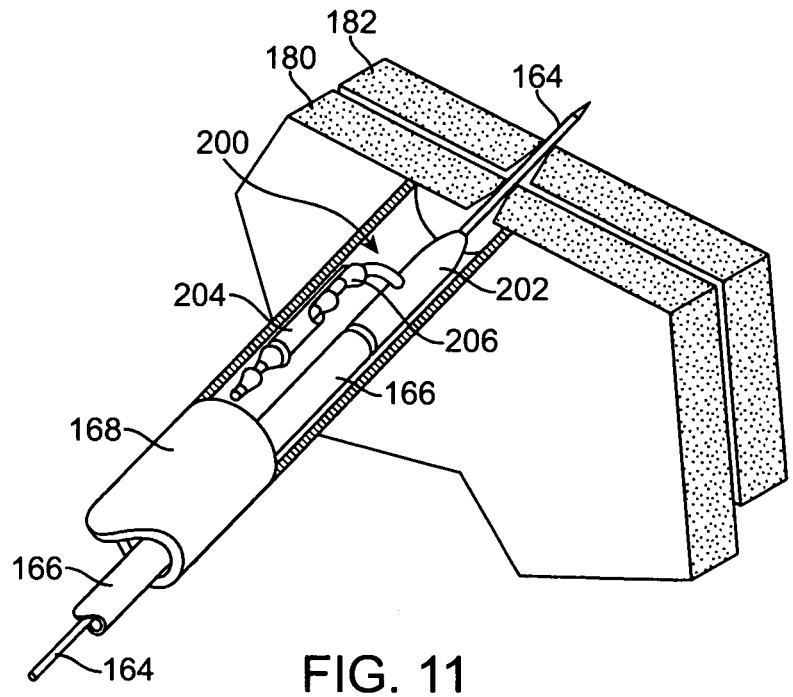
FIG. 11 is a perspective view with portions cut away of another fastener deployment assembly according to an embodiment of the invention in an early stage of deploying another fastener embodiment of the invention.
Figure 12:
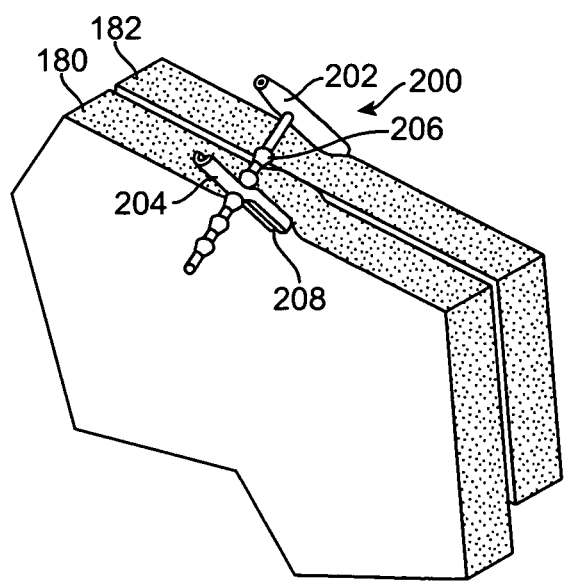
FIG. 12 is a perspective view showing the fastener of the assembly of FIG. 11 fully deployed and securely fastening a pair of tissue layers together.

FIG. 11 shows another fastener 200 embodying the present invention. The fastener 200 is illustrated in an initial stage of deployment by the tissue piercing deployment wire 164, the pusher 166, and the guide tube 168 to fasten tissue layers 180 and 182 together. FIG. 12 shows the fastener 200 after deployment fastening tissue layers 180 and 182 together. The fastener 200 may be deployed as previously described in connection with FIGS. 5-9.

The fastener 200 includes a first member 202, a second member 204, and a connecting member 206. The connecting member 206 takes the form of a beaded chain and the second member is bifurcated at 208 to permit the second member 204 to be positioned between any pair of beads of the connecting member 204. This renders the length of the connecting member 206 between the first and second members 202 and 204 adjustable to accommodate tissue layers of various densities and thicknesses.

Figure 13:
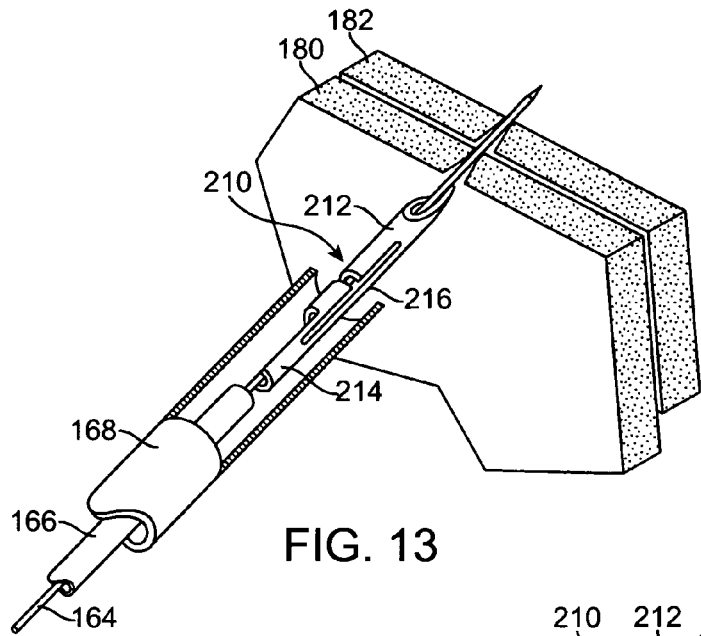
FIG. 13A is a perspective view, to an enlarged scale, of the fastener of FIG. 13.
Figure 13A:
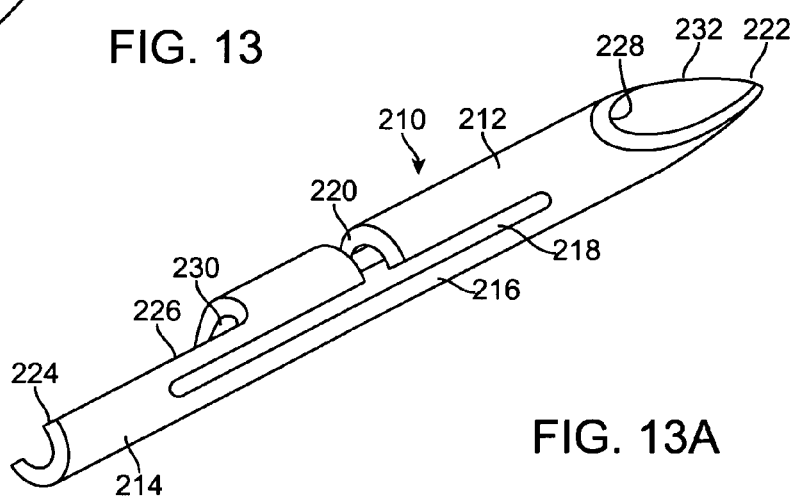

FIG. 13 shows another fastener 210 embodying the present invention. The fastener 210 is illustrated in an initial stage of deployment by the tissue piercing deployment wire 164, the pusher 166, and the guide tube 168 to fasten tissue layers 180 and 182 together. FIG. 13A shows the fastener 210 in greater detail.

The fastener includes a first member 212, a second member 214, and a connecting member 216. The first member 212, second member 214, and connecting member 216 are integrally formed from a same tubular member stock of material. The fastener 212 may be formed of plastic or metal, such as stainless steel or nitinol. As will be seen hereinafter, it is preferred that the fastener 212, and all other fasteners embodying the present invention be formed of a material which is capable of returning to a desired shape or assuming a desired shape after being bent. Many plastics and metals are capable of providing this function to render the first member 212 and second member 214 self-deployable for fastening the tissue layers 180 and 182.

As may be best seen in FIG. 13A, the connecting member 216 is formed of a strip of a tubular member formed by a pair of longitudinal substantially parallel, substantially co-extensive cuts within the tubular body of the fastener 210. One such cut 218 is illustrated in the drawing, and the other such cut is formed along the opposite side of the tubular body. The first member 212 and second member 214 are formed by a substantially transverse circumferential cut 220 between the substantially parallel co-extensive cuts 218. The substantially parallel substantially co-extensive cuts 218 begin spaced from a first end 222 of the fastener 210 and terminates spaced from a second end 224 of a second end. The first member 212 and second member 214 are thus tubular member sections between the circumferential cut 220 and the tubular member first end 222 and second end 224. The fastener 210 still further includes an elongated notch 226 extending from the second end 224 of the fastener 210 and extends towards the second end 222 substantially diametrically opposite and juxtaposed to a portion of the connecting member 216. The notch 226 terminates proximal to the transverse circumferential cut 220.

The foregoing results in fastener 210 including a through channel 228 within the first member 212 and a through channel 230 within the second member 214 to permit the fastener 210 to be slidingly received on the tissue piercing wire 164 as illustrated in FIG. 13. In addition, the fastener 210 at the first end 222 includes a pointed tip 232 which is formed by a sectioned portion of the tubular stock of the fastener 210.

As may be best seen in FIG. 13, when the fastener 210 is to be deployed, it is placed on the tissue piercing wire 164 with the first member 212 and second member 214 in line with one another. The tissue piercing wire 164 and fastener 210 are guided to their proper position adjacent tissue layer 180. Next, the tissue piercing wire 164 is advanced to pierce tissue layers 180 and 182 as illustrated in FIG. 13.

Figure 14:
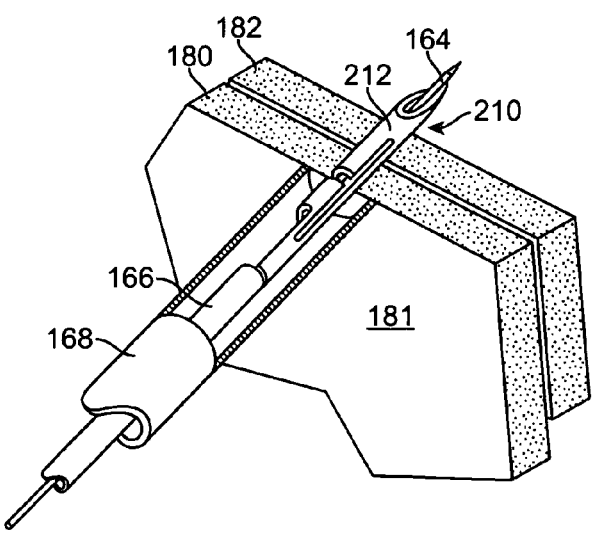
FIG. 14 is a perspective view of the assembly of FIG. 13 shown with the fastener being driven in the tissue layers to be fastened.

Next, as seen in FIG. 14, the pusher 166 is utilized to push the fastener 212 through the tissue layers 180 and 182 on the tissue piercing wire 164. As depicted in FIG. 14, the end of the first member 212 has just cleared the surface 181 of tissue layer 180.

Figure 15:
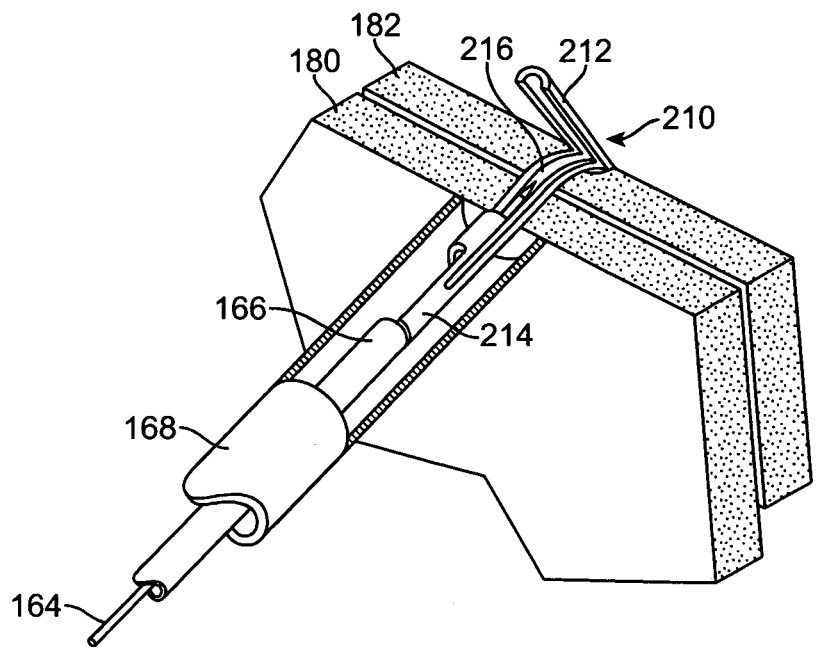
FIG. 15 is a perspective view of the assembly of FIG. 13 shown with the fastener extending through the tissue layers to be fastened and partially deployed.

Referring now to FIG. 15, when the pusher 166 pushes the fastener so that the first member 212 is through the tissue layer 182, the first member 212 is free to deflect to a preformed configuration with respect to connecting member 216. The first member 212 deflects as shown in FIG. 15 after the tissue piercing wire 164 is partially withdrawn as illustrated in FIG. 15. At this point, the second member 214 remains on the tissue piercing wire 164 and has not deflected to its preshaped configuration.

Figure 16:
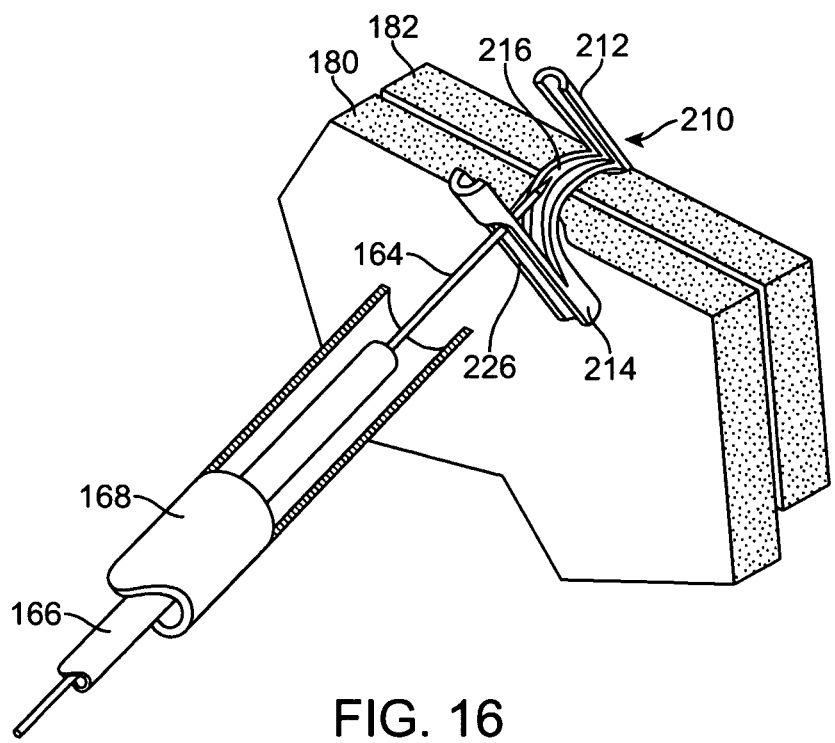
FIG. 16 is a perspective view of the assembly of FIG. 13 shown with the fastener initially fully deployed.
Figure 17:
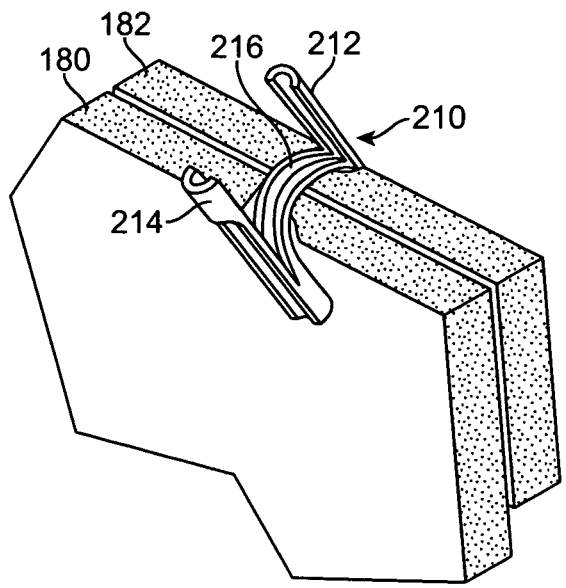
FIG. 17 is a perspective view showing the fastener of the assembly of FIG. 13 fully deployed and securely fastening a pair of tissue layers together.

As may be best seen in FIG. 16, a pusher 166 and most importantly the guide tube 168 are retracted to free the second member 214 to deflect to its preformed configuration. By virtue of the notch 226, the second member 214 is free to deflect as illustrated while on the tissue piercing wire 164. As illustrated in FIG. 16, the fastener 210 is in its deployed configuration. The first member 212 self-deployed with the partial retraction of the tissue piercing wire 164 and the second member 214 self-deployed with a retraction of the guide tube 168. With the fastener 210 thus deployed, the tissue piercing wire 164, pusher 166, and guide tube 168 may be fully retracted. This is illustrated in FIG. 17. As may be best seen in FIG. 17, the fastener 210 is deployed with the first member 212 and second member 214 in contact with opposite sides of tissues 180 and 182 and with the connecting member 216 extending between the first member 212 and second member 214 through the tissue layers 180 and 182. The shape memory material of the fastener 210 also permits the connecting member 216 to be provided with a preshaped arcuate configuration as shown to cause the connecting members 212 and 214 to securely fasten and pinch the tissue layers 180 and 182 together.

FIGS. 18-22 show another tissue fastening assembly 240 embodying the present invention. The assembly 240 includes the fastener 210 previously described with reference to FIG. 13A and the tissue fastening assembly of FIGS. 13-16.

Figure 18:
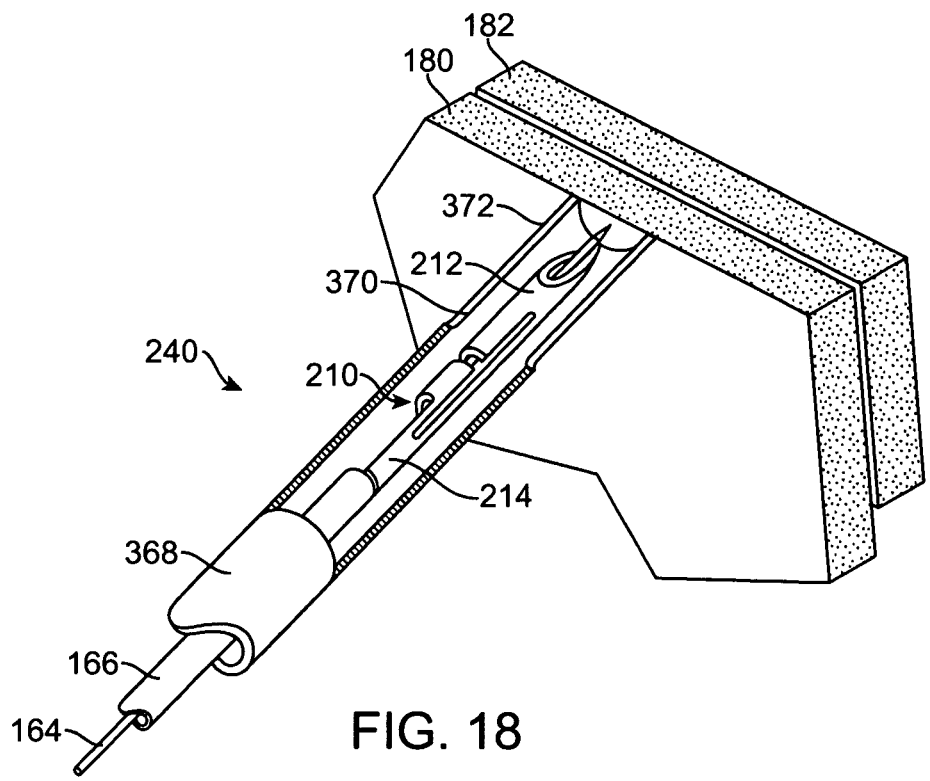
FIG. 18 is a perspective view with portions cut away of another fastener deployment assembly according to an embodiment of the invention in an early stage of deploying the fastener of FIG. 13.
Figure 19:
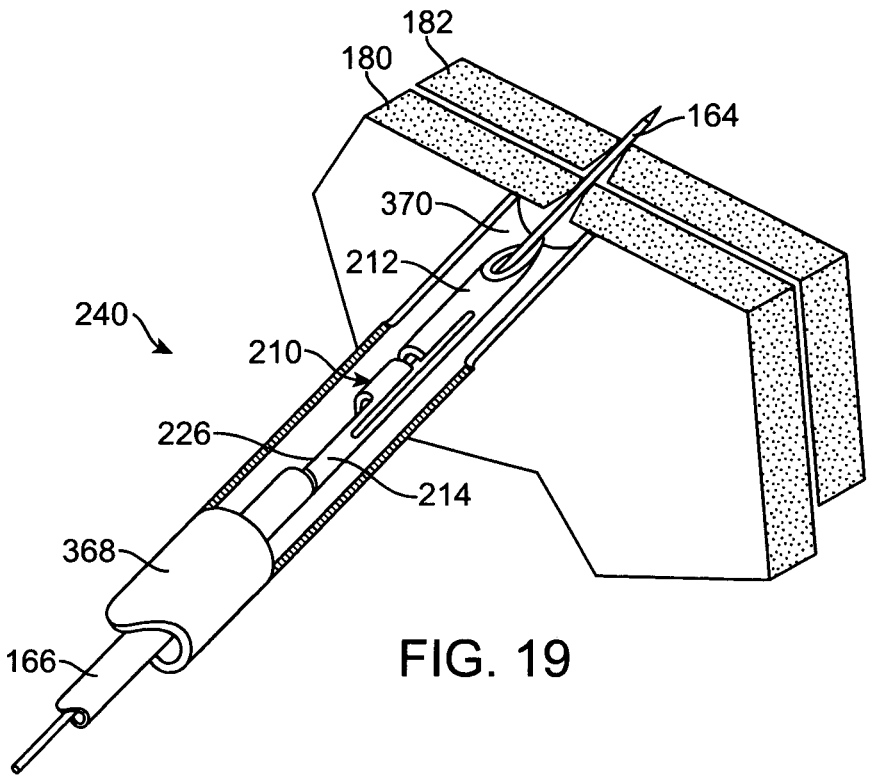
FIG. 19 is a perspective view of the assembly of FIG. 18 shown with the deployment wire driven through the tissue layers to be fastened.

In addition to the fastener 210, the assembly 240 includes the tissue piercing wire 164, the pusher 166, and a guide tube 368. The guide tube 368 is similar to the guide tube 168 previously described. However, a guide tube 368 includes a slot 370 at its distal end 372. The slot 372, as will be seen subsequently, permits the second member 214 to assume its deployed configuration before the first member 212 assumes its deployed configuration. FIG. 18 illustrates the assembly 240 in an early stage of deploying the fastener 210. FIG. 19 shows the assembly 240 wherein the tissue piercing wire 164 has been advanced to pierce the tissue layers 180 and 182 while the guide tube 368, the pusher 166, and the fastener 210 are held stationary. With the tissue piercing wire 164 piercing the tissue layers 180 and 182, the guide tube 368 may be partially retracted so that the notch 370 is adjacent the second member 214. By virtue of the notch 226, the second member 214 is permitted to assume its deployed configuration through the slot 370.

Figure 20:
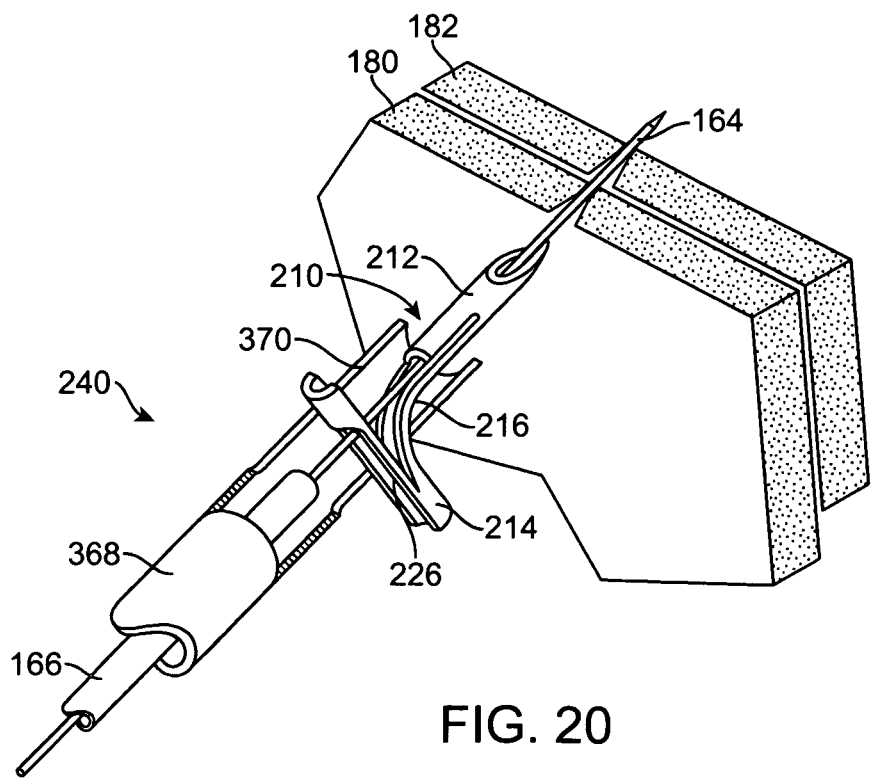
FIG. 20 is a perspective view of the assembly of FIG. 18 shown as in FIG. 19 but with the proximal end of the fastener being released into a deployed configuration before the fastener is driven into the tissue layers to be fastened.

FIG. 20 illustrates the second member 214 of the fastener 210 in its deployed configuration within the slot 370. As will be noted in FIG. 20, the connecting member 216 is permitted to assume its preshaped configuration and the second member 214 is permitted to slide along the tissue piercing wire 164 within the notch 226. With the second member 214 in its deployed configuration, the pusher 166 may now push the first member 212 through the tissue layers 180 and 182 on the tissue piercing wire 164.

Figure 21:
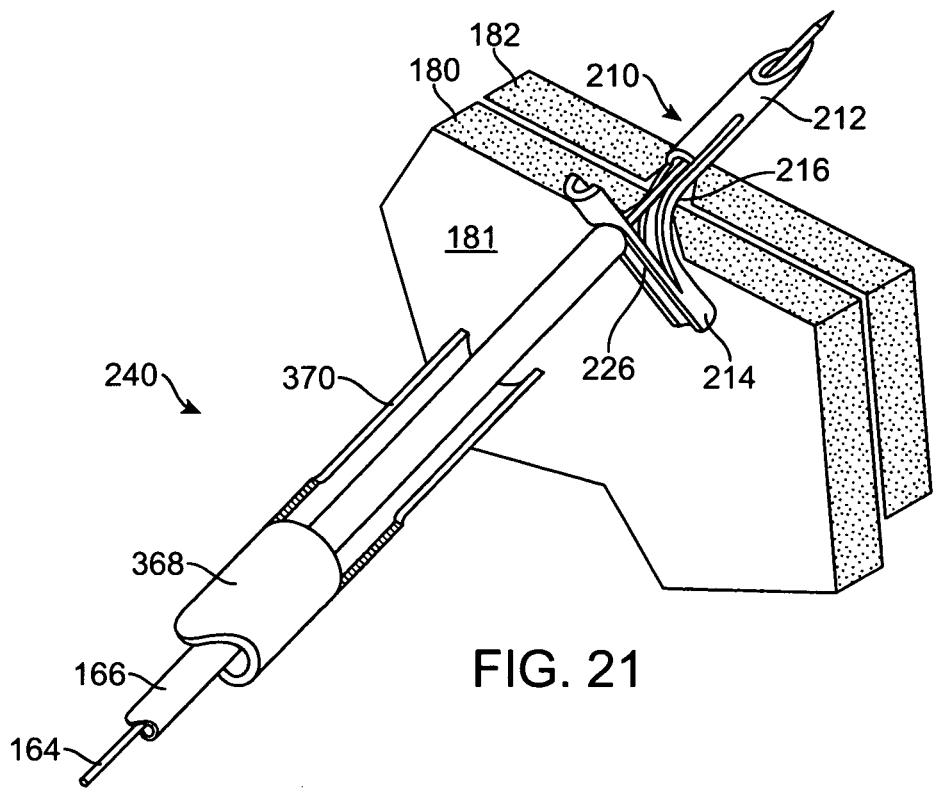
FIG. 21 is a perspective view of the assembly of FIG. 18 shown with the fastener extending through the tissue layers to be fastened.

FIG. 21 illustrates the fastener 210 with the first member 212 pierced through the tissue layers 180 and 182 and the second member 214 in its deployed configuration. The second member 214 is now against surface 181 of tissue layer 180.

Figure 22:
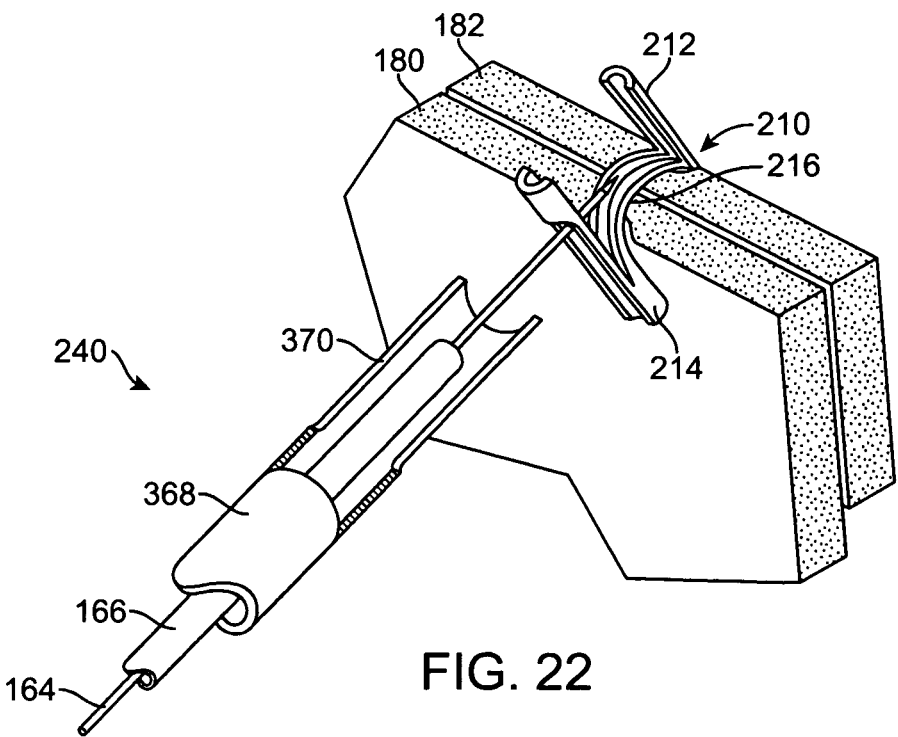
FIG. 22 is a perspective view of the assembly of FIG. 18 shown with the fastener initially deployed.

With the second member 214 first deployed, as may be seen in FIG. 22, the tissue piercing wire 164 may be partially retracted to free the first member 212 and to permit the first member 212 to assume its deployed configuration. At this point, the second member 214 is still on the tissue piercing wire 164.

Now that both of the first and second members 212 and 214 respectively are deployed, the tissue piercing wire 164, pusher 160, and guide tube 368 may be fully retracted to leave the fastener 210 in its deployed configuration.

Figure 23:
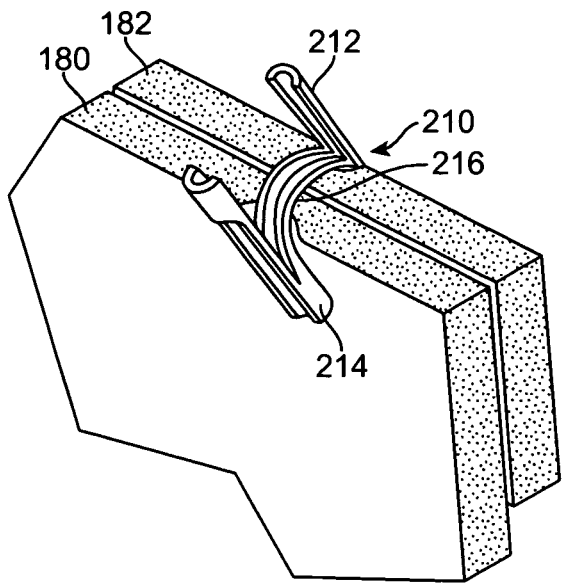
FIG. 23 is a perspective view showing the fastener of the assembly of FIG. 18 fully deployed and securely fastening a pair of tissue layers together.

FIG. 23 illustrates the fastener 210 in its deployed configuration after the tissue piercing wire 164, pusher 166, and guide tube 368 are fully retracted. Again, the tissue layers 180 and 182 are securely fastened together by the fastener 210 as previously described.

Figure 24:
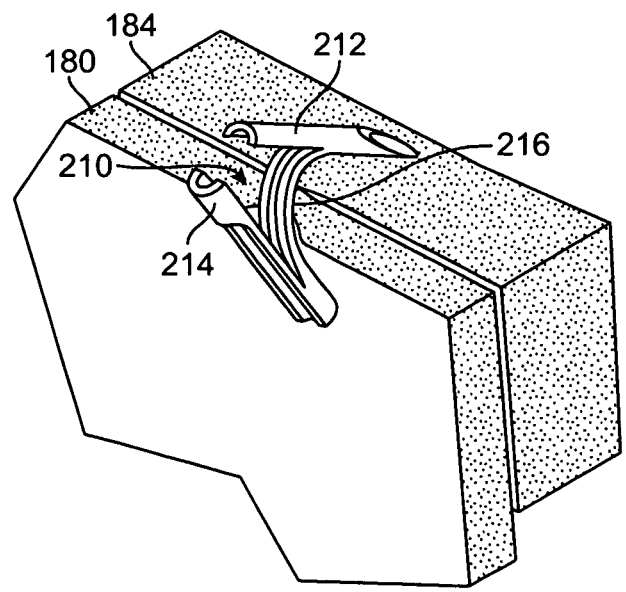
FIG. 24 is a perspective view of the fastener of FIG. 13 showing the fastener embedded within a layer of tissue.

FIG. 24 is a perspective view of the fastener 210 imbedded within a tissue layer 184 which is adjacent the tissue layer 180. Here it will be seen that the first member 212 of the fastener 210 is fully imbedded within the tissue layer 184. The fastener 210 may be deployed as illustrated in FIG. 24 by any one of the methods previously described with respect to FIGS. 13-16 and FIGS. 18-22. Once the tissue piercing wire 164 is withdrawn to free the second member 212, the second member 212 will become imbedded within the tissue 184. This illustrates the flexibility provided by the fasteners of the present invention for use with varying types of tissue.

Figure 25:
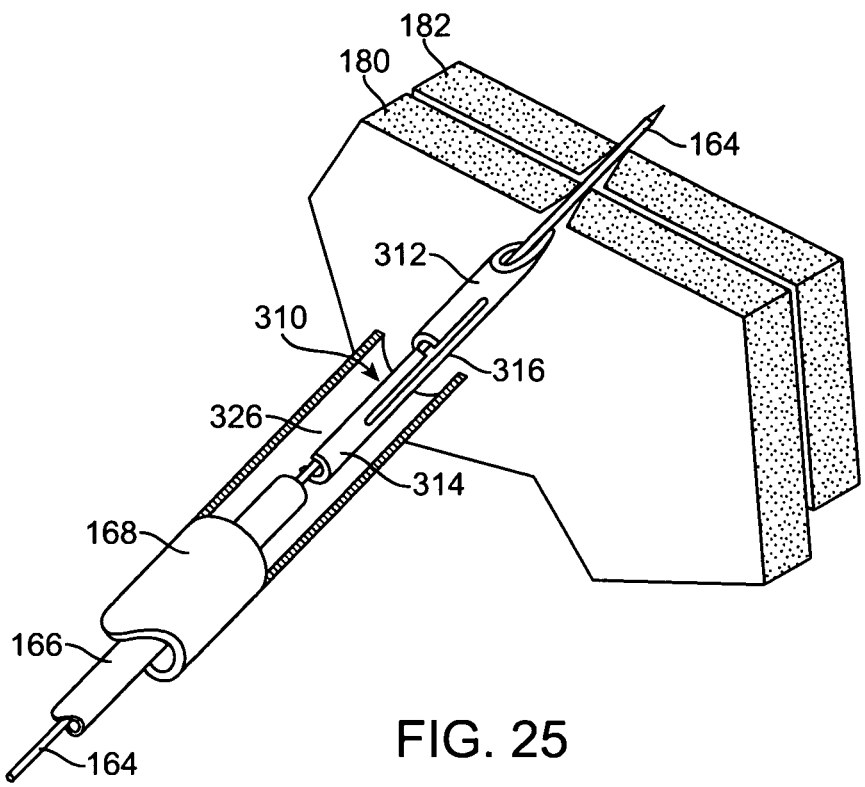
FIG. 25 is a perspective view with portions cut away of a fastener assembly according to an embodiment of the invention in an early stage of deploying a still further fastener embodiment of the invention.

FIG. 25 is a perspective view with portions cut away of a further fastener 310 embodying the present invention in association with the tissue piercing wire 164, the pusher 166, and the guide tube 168 for fastening tissue layers 180 and 182 together. The fastener 310 includes a first member 312, a second member 314, and a connecting member 316. The fastener 310 is essentially identical to the fastener 210 previously described except that its notch 326 extends the entire longitudinal length of the second member 314. As a result, the second member 314 may assume its deployed configuration off of the tissue piercing wire 164. In other words, when the second member 314 deploys, it will be, by virtue of the continuous notch 326, free of the tissue piercing wire 164. As a result, the tissue piercing wire 164 need not be fully retracted to free the second member 314 from the tissue piercing wire 164 after it has been deployed.

Figure 26:
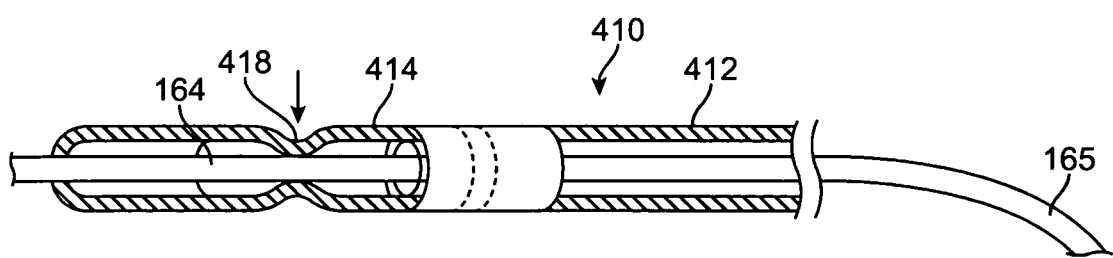
FIG. 26 is a side view, partly in cross-section of another fastener embodiment of the invention which provides resistance to relative movement between the fastener and a deployment wire.

FIG. 26 is a side view, partly in cross-section, of another fastener embodiment 410 of the invention. The fastener 410 includes a first member 412, a second member 414, and a connecting member which cannot be seen in the figure. One of the first and second members 412 and 414 includes a restrictor or crimp 418. Here it may be seen that the second member 414 includes the crimp 418. The depth of the crimp 418 is controlled to exert a controlled amount of pressure against the tissue piercing wire 164. The controlled pressure by the crimp 418 on the tissue piercing wire 164 provides controlled resistance to movement between the fastener 410 and the tissue piercing wire 164. This may provide a more "in control" feel between the fastener 410 and tissue piercing wire 164 during the deployment of the fastener 410. It may also be noted in FIG. 26 that the deployment wire 164 has a bent or curved tip 165. The bent tip 165 renders the development wire 164 steerable to aid in guiding the fastener to its intended location within the body.

Figure 27:
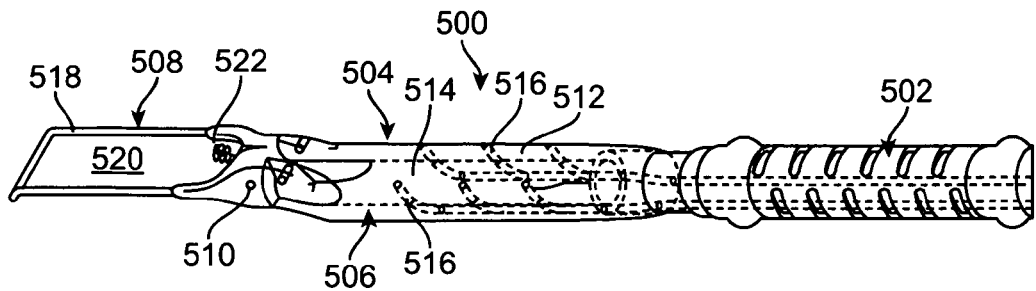
FIG. 27 is a perspective side view, partly in phantom of a gastroesophageal flap valve restoration device embodying the present invention shown in an initial state before use.
Figure 28:
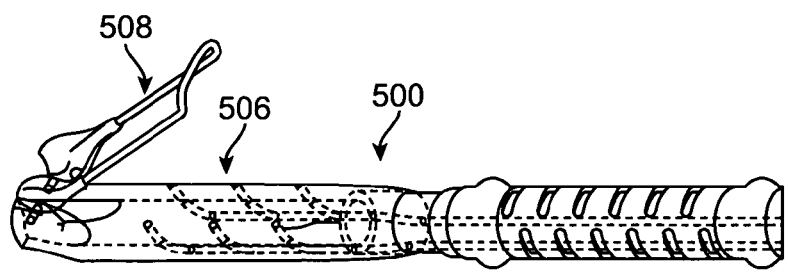
FIG. 28 is another perspective side view, partly in phantom of the gastroesophageal flap valve restoration device of FIG. 27 embodying the present invention shown in an intermediate state during use.
Figure 29:
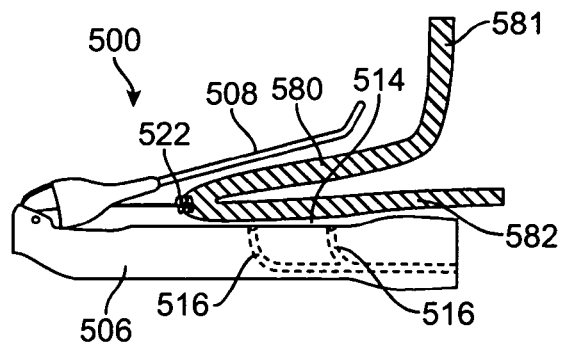
FIG. 29 is a side view, partly in cross-section of the gastroesophageal flap valve restoration device of FIG. 27 shown forming a gastroesophageal flap valve from stomach tissue prior to delivery of a fastener to maintain the flap valve.

Referring now to FIGS. 27-29, they illustrate a tissue fixation assembly 500 which may utilize the fasteners and fastener deployment assemblies previously described and embodying the present invention to advantage. Although the fasteners and deployment assemblies previously described and embodying the present invention may be used in numerous applications, the assembly 500 of FIGS. 27-29 is particularly configured as a transoral gastroesophageal flap valve restoration device for restoring a gastroesophageal flap valve.

With initial reference to FIG. 27, the device of FIG. 27 generally includes a longitudinal member 502 and a tissue shaper 504 carried at the distal end of the longitudinal member 502. The tissue shaper 504 and longitudinal member 502 are dimensioned for passing through the esophagus for transoral placement into a stomach.

The tissue shaper 504 includes a first arm 506 and a second arm 508. The first arm 506 and second arm 508 are hingedly coupled together at a hinge point 510. The first arm includes a fastener director 512. As will be seen hereinafter, stomach tissue layers to be fastened together may be shaped by the tissue shaper 504 by the first arm 506 and second arm 508 confining the stomach tissue layers therebetween. The first arm 506 has a tissue engaging surface 514. The first arm further includes a plurality of fastener directing channels 516. The fastener directly channels 516 communicate with the tissue engaging surface 514. Each of the fastener directing channels 516 serves to direct a fastener into the tissue layers to be fastened together. Accordingly, the fastener directing channels 516 are configured and dimensioned for receiving a tissue fastener such as, for example, any one of the fasteners previously described herein and embodying the present invention.

The second arm 508 is a frame structure 518. The frame structure 518 defines an opening 520 to permit the fasteners to be driven through the tissue layers while being held between the first arm 506 and second arm 518.

The tissue shaper 504 further includes a tissue gripper 522. The tissue gripper 522 takes the form of a helical coil that grips the stomach tissue. As will be seen hereinafter, the tissue gripper is arranged to pull the stomach tissue into and between the first and second arms 506 and 508.

Referring now to FIG. 28, it illustrates the configuration of the device 50 when shaping stomach tissue into a gastroesophageal flap valve. Here it may be seen that the second arm 508 has been pivoted relative to the first arm 506. This permits stomach tissue pulled between the arms 506 and 508 to be shaped as a gastroesophageal flap. FIG. 29 shows this in greater detail. Here it may be seen that the tissue gripper 522 has gripped stomach tissue 581 to form tissue layers 580 and 582 in the shape approximating a gastroesophageal flap. With the stomach tissue 581 drawn into and between the first arm 506 and second arm 508 with the tissue engaging the tissue engaging surface 514, fasteners may now be directed through the channels 516 and deployed for fastening stomach tissue layers 580 and 582 together. A plurality of channels 516 are provided to enable a plurality of fasteners to be deployed.

In deploying the fasteners, the fastener directing channels 516 may serve as guide tubes for guiding tissue piercing wires and pushers as previously described for deploying the fasteners. Alternatively, fastener guide tubes taking the form, for example, of guide tube 168 previously described, may also be utilized and directed by the channels 516 in the deployment of the fasteners.

Once the tissue layers 580 and 582 are fastened together, they will be maintained in the folded configuration to approximate a gastroesophageal flap valve. The helical coil 522 may then be rotated to disengage from the tissue and the first and second arms 506 and 508 may be pivoted back to an in line configuration for retraction from the stomach and esophagus to complete the gastroesophageal flap valve restoration procedure.

Because in this embodiment, the contacting tissue layers held by the fastener are both serosa tissue, the tissue layers will eventually grow together. Hence, the fasteners of the present invention may be formed of reabsorbable material which, after sufficient time to permit fusion of the tissue layers, will be absorbed by the body.

Figure 30:
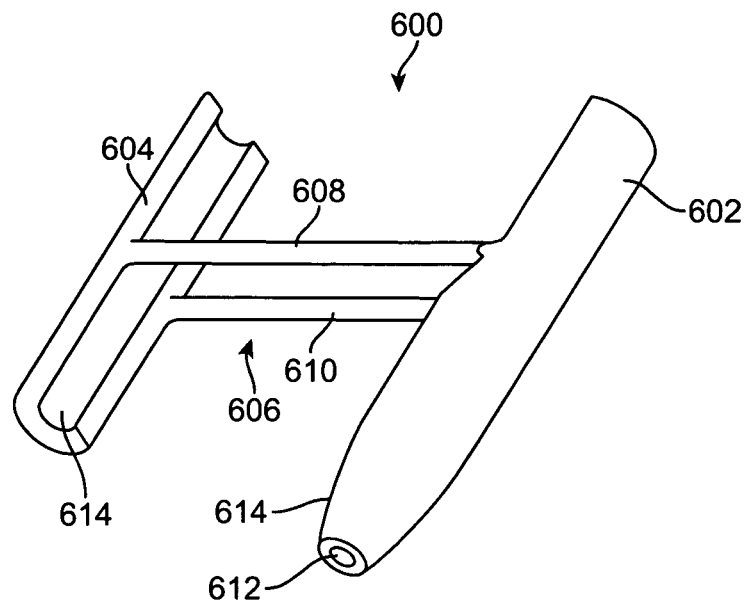
FIG. 30 is a perspective view of another fastener embodiment of the present invention.
Figure 31:
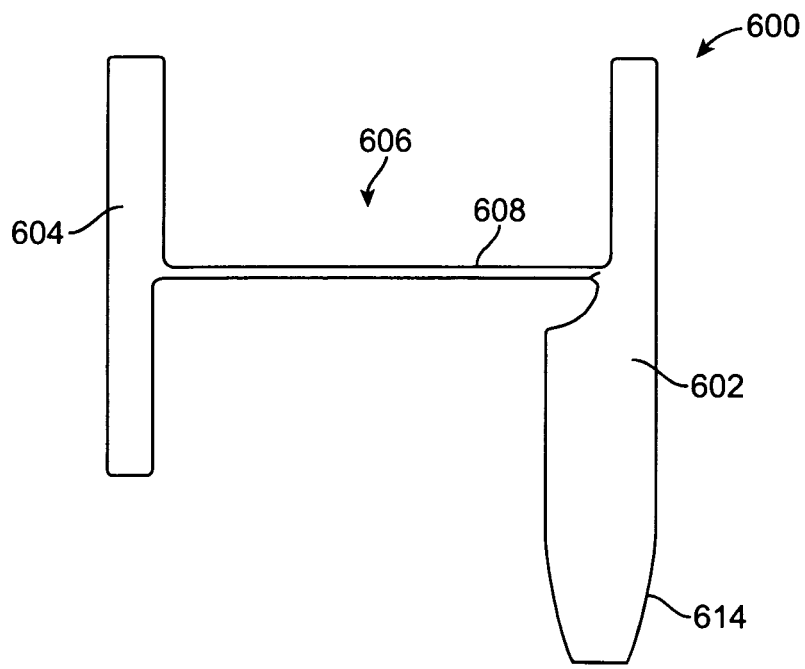
FIG. 31 is a top plan view of the fastener of FIG. 30.

Referring now to FIGS. 30 and 31, they illustrate still another fastener 600 according to an embodiment of the invention. The fastener 600 generally includes a first member 602, a second member 604, and a connecting member structure 606. As may be noted in FIGS. 30 and 31 the connecting member structure includes a plurality of connecting members 608 and 610. The connecting members 608 and 610 connect the first member 602 to the second member 604.

The first member 602 is cylindrical and the second member 604 is a cylindrical half-section. Each has a longitudinal through channel 612 and 614. The through channel 614 is a through bore which is dimensioned to be a slidingly received on a tissue piercing deployment wire. The channel 614 is dimensioned to be optionally carried on the deployment wire prior to deployment.

The first member 602 also includes a conical pointed tip 614.

The fastener 600 may be formed of any of the plastic or metal material previously described. As may be further noted in FIGS. 30 and 31 the connecting members 600 and 610 are relatively thin to render the connecting member structure 606 readily bendable for ease of deployment. The connecting member structure is further rendered bendable of course by the nature of the plastic or metal material from which the fastener 600 is formed.

Figure 32:
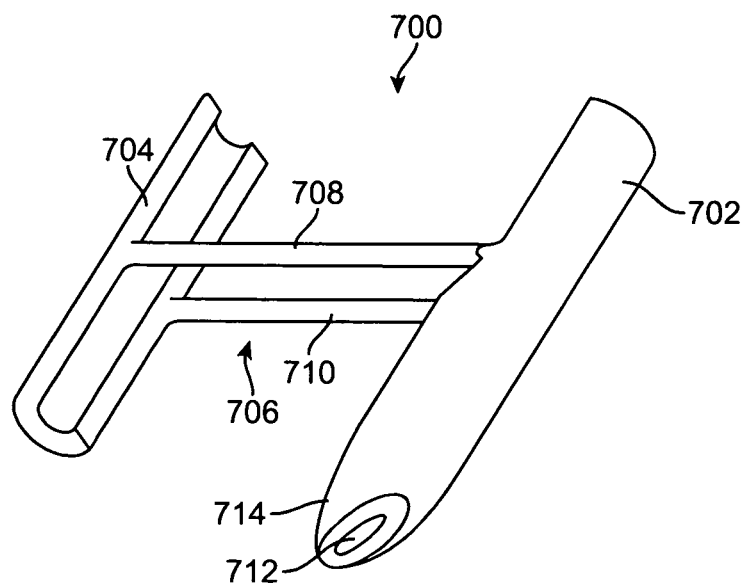
FIG. 32 is a perspective view of still another fastener embodiment of the present invention.
Figure 33:
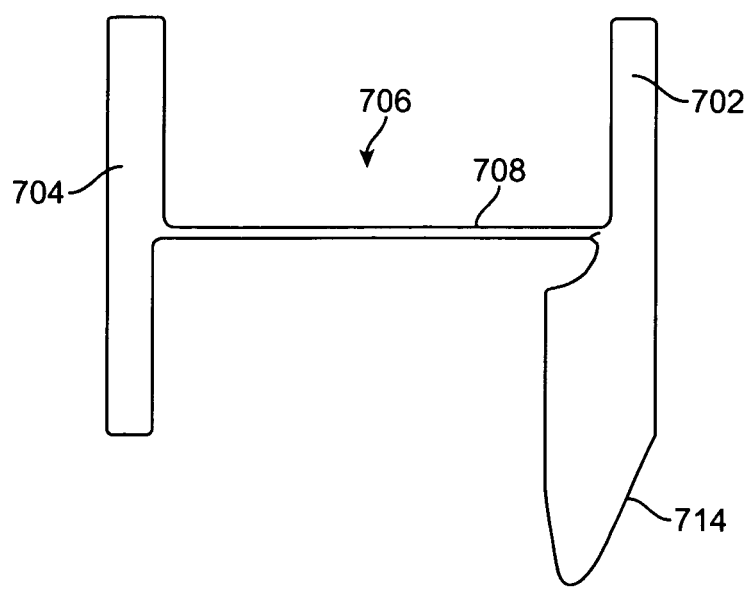
FIG. 33 is a top plan view of the fastener of FIG. 32.

Referring now to FIGS. 32 and 33, they illustrate another fastener 700 embodying the present invention. As with the previous fastener, the fastener 700 includes a cylindrical first member 702, cylindrical half-section 704 and a connecting member structure 706. The connecting member structure 706 includes connecting members 708 and 710. Here however, the pointed tip 714 takes the form of a tapered section of the first member 702.

As in the previous embodiment the first member 702 of the fastener 700 may be slidingly received on a deployment wire. The deployment wire may be received by a bore 712. The fasteners 600 and 700 may be deployed as previously described.

While particular embodiments of the present invention have been shown and described, modifications may be made, and it is therefore intended in the appended claims to cover all such changes and modifications which fall within the true spirit and scope of the invention.

What is claimed is:

1. A fastener for use in a mammalian body, comprising;
a first member;
a second member;
the first and second members having first and second ends and one end of both the first member and the second member have a pointed tip and the pointed tips point in opposite directions;
a connecting member fixed to each of the first and second members intermediate the first and second ends and extending between the first and second members;
the first and second members being separated by the connecting member, the second member being movable on the connecting member so that a length of the connecting member between the first and second members is adjustable;
both of the first and second members having a longitudinal axis and a through channel along the axis arranged to be slidingly received on one tissue piercing deployment wire; and
wherein the through channels are arranged to be slidingly received on the one tissue piercing deployment wire and wherein the connecting member is flexible permitting the first and second members to be in line with each other on the one tissue piercing deployment wire, the first and second members being mounted to only the one tissue piercing deployment wire and no other wire.

2. The fastener of claim 1 wherein the connecting member is flexible permitting another one of the first and second members to be next to the one of the first and second members when the one of the first and second members is on the tissue piercing deployment wire.

3. The fastener of claim 1 wherein the pointed tip is conical.

4. The fastener of claim 1 wherein the pointed tip comprises a sectioned portion.

5. The fastener of claim 1 wherein the pointed tip is a dilation tip.

6. The fastener of claim 1 wherein the through channel comprises a through bore.

7. The fastener of claim 1 wherein the through channels are through bores.

8. The fastener of claim 1 wherein the fastener is at least partially radiopaque.

9. The fastener of claim 1 wherein the connecting member is formed of elastic material.

10. The fastener of claim 1 wherein the first member, the second member, and the connecting member are all formed of plastic material.

11. The fastener of claim 10 wherein the first member, and the connecting member are formed in one piece.

12. The fastener of claim 11 wherein one end of the one of the first and second members further includes a pointed tip.

13. The fastener of claim 12 wherein the pointed tip comprises a truncated cone.

14. The fastener of claim 12 wherein the through channel comprises a through bore.

* * * * *